United States Patent
Gupta et al.

(10) Patent No.: US 11,568,964 B2
(45) Date of Patent: Jan. 31, 2023

(54) SMART SYNTHESIZER SYSTEM

(71) Applicant: Praxify Technologies, Inc., Palo Alto, CA (US)

(72) Inventors: Abhijit Manohar Gupta, Pune (IN); Mohan Rao, Pune (IN)

(73) Assignee: Praxify Technologies, Inc., Palo Alto, CA (US)

( * ) Notice: Subject to any disclaimer, the term of this patent is extended or adjusted under 35 U.S.C. 154(b) by 308 days.

(21) Appl. No.: 15/831,684

(22) Filed: Dec. 5, 2017

(65) Prior Publication Data

US 2018/0158539 A1 Jun. 7, 2018

(30) Foreign Application Priority Data

Dec. 5, 2016 (IN) .............................. 201621041462

(51) Int. Cl.
*G16H 10/60* (2018.01)
*G16H 40/20* (2018.01)
*G16H 15/00* (2018.01)

(52) U.S. Cl.
CPC ............. *G16H 10/60* (2018.01); *G16H 15/00* (2018.01); *G16H 40/20* (2018.01)

(58) Field of Classification Search
CPC ........ G16H 10/60; G16H 15/00; G16H 40/20; G06F 19/30; G06F 19/32; G06F 19/34; G06Q 50/22; G06Q 50/24
See application file for complete search history.

(56) References Cited

U.S. PATENT DOCUMENTS

| | | | | |
|---|---|---|---|---|
| 7,379,885 B1* | 5/2008 | Zakim | ................... | G06F 19/325 705/2 |
| 2014/0350961 A1* | 11/2014 | Csurka | ................... | G16H 10/60 705/3 |
| 2015/0149212 A1* | 5/2015 | Rolia | ..................... | G06Q 50/22 705/3 |
| 2015/0234987 A1* | 8/2015 | Laing | ..................... | G06F 19/00 705/3 |
| 2016/0275254 A1* | 9/2016 | Mahoney | ............... | G16H 40/67 |
| 2017/0124269 A1* | 5/2017 | McNair | .................. | G16H 50/20 |

* cited by examiner

*Primary Examiner* — Maroun P Kanaan

(74) *Attorney, Agent, or Firm* — GTC Law Group PC & Affiliates

(57) ABSTRACT

Methods, systems, and apparatus, including computer programs encoded on computer storage media for generating a patient profile. One method includes generating a patient profile corresponding to a patient that comprises profile data items and profile data parameters. Generating a synthesized context-aware rendition of a patient summary from the profile data items and the profile data parameters. Mapping doctor specialties and data workflows in relation to the synthesized context-aware rendition of the patient summary.

23 Claims, 1 Drawing Sheet

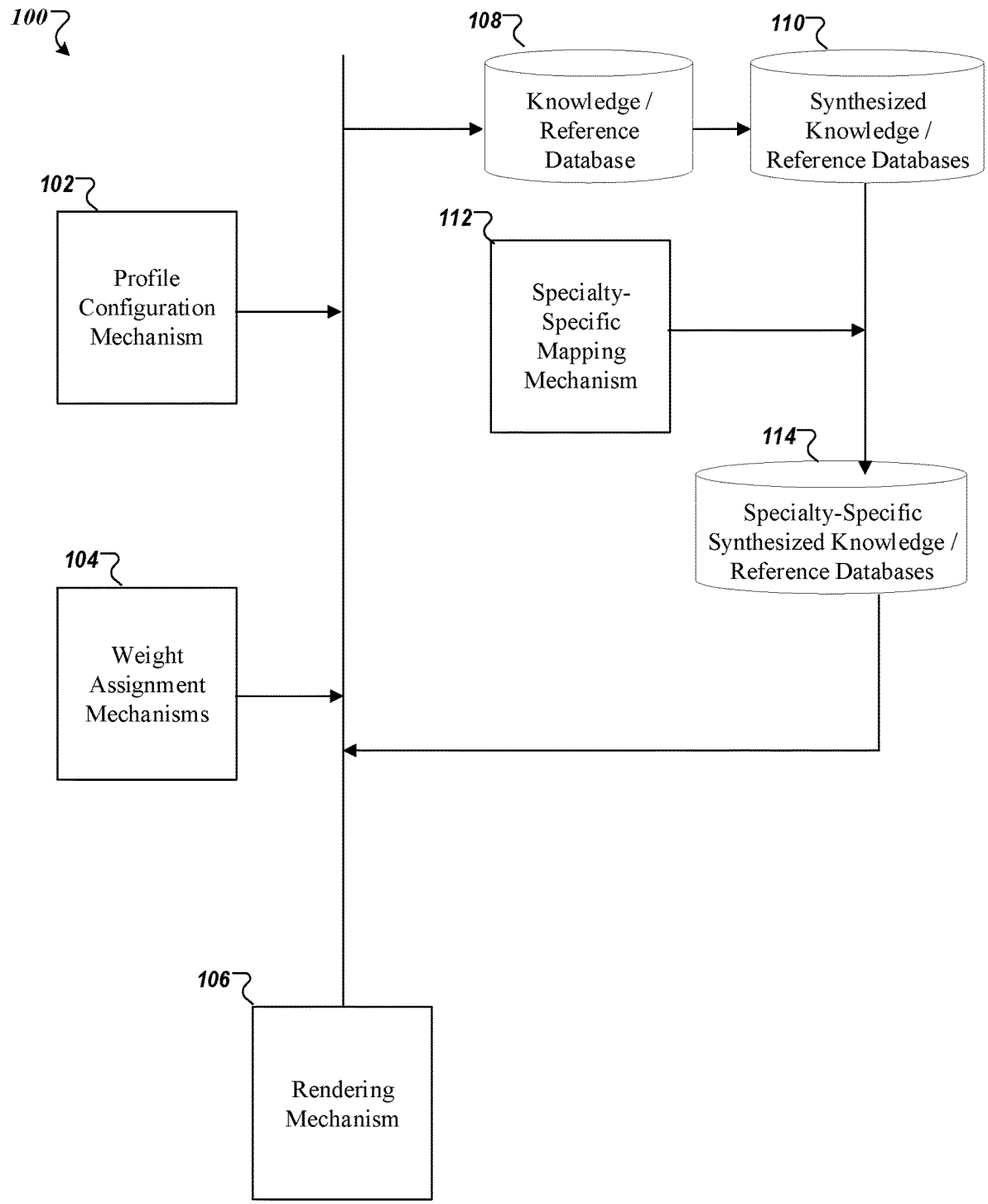

SMART SYNTHESIZER SYSTEM

CROSS-REFERENCE TO RELATED APPLICATION

This application claims priority under 35 U.S.C. § 119 to Indian Patent Application No. 201621041462, filed on Dec. 5, 2016, which contents is hereby incorporated by reference in its entirety.

BACKGROUND

This specification relates generally to the field of information systems, computational systems, databases, networking systems, and communication systems.

SUMMARY

This specification relates to the field of healthcare information, healthcare technology, healthcare management, electronic medical records, electronic health records, decision support systems and patient centered care.

Medical practice entails activities in relation to human health and body, understanding and diagnosing various factors affecting human health and body, surgical procedures, examination procedures, diagnostic procedures, prognosis procedures, and similar activities. Qualified medical professionals are equipped to deal with various facets of medical practice; in relation to the academic qualification that they have reached, and in relation to the professional experience that they have gained.

The terms medical record, health record, encounter and medical chart are used somewhat interchangeably to describe the systematic review and documentation of a single patient's medical or health journey including a patient's history, diagnosis, prognosis, symptoms, vitals, review of systems, physical examination, medications, lab and diagnostics, allergies, surgical procedures and care. These factors include across time not just within one particular health care provider setting, but also covering multiple health care providers and the multiple health care providers' interactions with the respective patient in context.

Medical records include a variety of notes and data relating to doctor-patient interaction, doctor's interpretation of patient's complaints, diagnosis, prognosis, investigations and treatment plans. This data could include signs and symptoms data, review of various body systems data, examination data, vitals data, diagnosis data, medical decision making data, medical history data, family history, social history, previous surgical procedures and hospitalizations, any specific historical data of medicines taken, allergies, chronic and acute problems, lab reports, radiology images and reports' data, other investigation results' data, input/output data, and drugs and immunization administration data and medication data. In addition, this data can include prognosis data, visit notes, insurance data, demographics, other relevant health histories, genomic data, data from wearables and other medical devices, and other similar types of data. As such, it is essential for both the doctor and the patient to review and maintain complete and accurate medical records for ensuing accurate diagnosis and treatment also from a general health perspective, a wellness perspective, and a legal perspective.

Medical records are used to understand the patient's current health status and past health history to ensure patient wellness. In addition, a doctor may review medical records to identify patient's diagnosis and provide/recommend relevant treatment protocols to a patient or fellow care providers for treating patients. Medical records can also be used as an aid to supplement the judgement and decision of a doctor/care provider. Medical records are also used in a system to capture data of a patient at various stages of his/her life and is used for a variety of medical and analytical purposes.

The types of personal health information that can be included in the medical records may cover the following: patient demographics information including, but not limited to, name, gender, birth date, blood type, race, ethnicity, marital status, address/geographical location, emergency contact information; complete history of patients past visit histories; date of last physical exam; dates and results of tests and screenings; major illnesses and surgeries, with dates; a list of medicines, dosages and how long they are being taken; any allergies and its reactions; any chronic/acute diseases and treatment plans; any history of illnesses in your family; dates and results of lab tests, imaging tests, and screenings; social history, family history; immunizations; risk assessments; care plans; vitals; data from wearables; genomic data; and, various clinical assessments and scores.

In general, one innovative aspect of the subject matter described in this specification can be embodied in methods that include the actions of generating a patient profile corresponding to a patient that comprises profile data items and profile data parameters. Generating a synthesized context-aware rendition of a patient summary from the profile data items and the profile data parameters. Mapping doctor specialties and data workflows in relation to the synthesized context-aware rendition of the patient summary.

Other embodiments of this aspect include corresponding computer systems, apparatus, and computer programs recorded on one or more computer storage devices, each configured to perform the actions of the methods. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

The foregoing and other embodiments can each optionally include one or more of the following features, alone or in combination. In particular, one embodiment includes all the following features in combination. In some implementations, the method includes, determining weighting assignments in relation to a context. In response to determining the weighting assignments in relation to the context, assigning weights to the profile data items, the profile data parameters, and knowledge/reference data items. The method can further include wherein determining the weighting assignments is determined based on a frequency of use, a latest use, determination of various heat maps to understand usage and behavior, location, specialty, and current condition of the patient.

The method can further include generating an interactive time-line view for a doctor-patient interaction from an observation profile. The method can further include wherein the observation profile changes in vitals, inputs, outputs in response to change in dosage of prescribed medicine, in response to change in filtering parameters for labs, vitals, and diagnostics. The method can further include determining a location of a doctor corresponding to the patient profile assessing a smart synthesizer system, wherein factors in determining the location of the doctor include care settings, seasons, external conditions, and seriousness of the condition of the patient.

The method can further include, storing, in an information database, journal information relating to diseases and treatment plans for the diseases, and case studies' information relating to the disease and treatment plans. The method can further include displaying, on the interactive time-line view, the changes in vitals, intake output, labs, or similar data in an empirical format and a predictive format.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 1 illustrates a block diagram of the smart synthesizer system.

Like reference numbers and designations in the various drawings indicate like elements.

DETAILED DESCRIPTION

A care management system typically includes comprehensive medical records of patients and set of procedures and protocols that a doctor prescribes for a patient. In its electronic format, patient centered electronic medical record systems involve all the aspects of patient and illness/disease management, steps pertaining to which are described above and may generally be referred to during a patient-doctor interaction or for treating patients or for evolving better treatment protocols for future patients. For a doctor to review and record all aspects or facets of a patient, during the doctor-patient interaction, it is imperative that such patient centered electronic medical record systems be intuitive towards the workflows of that particular doctor and keep in context the various aspects of patient's demographic and medical information. It is imperative that these systems provide patient medical information views to clinicians such that they spend as little time as possible to find relevant information to ensure better diagnosis and medical decision making for treatment protocols and document important facets of the patient's encounter, and focus more on patient care as much as possible. Intuitiveness in this case means the ability of the system to understand how a clinician practices, learn from how the clinician practices, and be able to provide the right workflow, so that the clinician does not waste time in searching for information relevant in the context of the patient and his/her history and for documenting a patient record.

Typically, a patient can be profiled in terms of demographics, medical history, family history, social history, current context (relating to season, epidemic, travel history, and the like), previous surgeries' history, investigations, vitals, current and previous problems, allergies, immunizations, and the like.

In at least one context of patient centered electronic medical record systems, a 'doctor-patient interaction' is meant to include the steps of understanding patient reported complaints, reviewing patient's medical records in the context of the complaints and condition, documenting history of present illnesses, to reviewing of body systems, to doing physical examination of the patient, and to diagnosis to treatment plan to prognosis. In this context, it is important that the system used in correlation with this doctor-patient interaction is ready to 'understand' the interaction.

In some implementations, it is important that the system is context-aware so that it understands the doctor correctly in terms of pre-defined parameters.

In some implementations, it is important that the system is context-aware so that the system understands the patient correctly in terms of pre-defined parameters.

In some implementations, it is important that the system is context-aware so that it understands the patient's previous records and histories correctly in terms of pre-defined parameters.

In some implementations, it is important that the system is context-aware so that it understands the doctor-patient interaction correctly in terms of pre-defined parameters.

In some implementations, it is important that the system is context-aware so that it understands the location and seasons correctly in terms of pre-defined parameters.

In some implementations, it is important that the system is context-aware so that it understands the demographic correctly in terms of pre-defined parameters.

In some implementations, it is important that the system is context-aware so that it understands how the doctor is interacting with the patient, reviewing medical records and documenting in the patient centered electronic medical record system in terms of pre-defined parameters.

In some implementations, it is important that the system is context-aware so that it understands the current condition or state of the patient while documenting in the patient centered electronic medical record system in terms of pre-defined parameters.

In some implementations, it is important that the system is context-aware so that it understands which data set (ex vitals, lab results, etc.) of the medical record should be promoted of the patient while reviewing patient medical records and documenting in the patient centered electronic medical record system in terms of pre-defined parameters.

In some implementations, it is important that the system is context-aware so that it understands which actions (e.g. add a particular problem, suggest a particular test, etc.) of the medical record should be promoted of the patient while documenting in the patient centered electronic medical record system in terms of pre-defined parameters.

It is important that an intelligent and intuitive system and method be configured and designed so that a doctor is enabled and empowered to interact with the system in a context-aware manner. Therefore, there is a need to make the system and method context-aware and context-ready for a doctor to interact with it.

With the advent of Internet of Things (JOT) and mobility, wearable devices and sensors have become ubiquitous in nature. Doctors today are facing issues with understanding contexts from trillions of bytes of information that they receive from their patients. The vastness of this data needs to be interpreted by intelligent systems, and has to be presented to a doctor in a manner, which will make logical sense for decision-making. This intelligent system needs to be aware of various contexts in which these datasets were captured by these devices. Those contexts need to be interpreted in real time to aid the doctor to not take unnecessary interventions or measures, which will increase healthcare costs.

Also, each doctor has his/her own way of practicing and consuming patient data. The data needs to communicate to the doctor, what answers he/she is looking for to take real time decisions at point-of-care. This method of synthesizing data with various contexts and presenting it to the doctor is one of the premises of this specification.

For example, a neurologist taking a round at an NICU to see a mid-aged male trauma patient, and sees his last 24 hours of vitals, then reviews last updated lab results, searches for a particular medication order, and sees what happened to vitals post that medication, looks for nursing notes to find any adverse events, and then goes to documenting the encounter. The machine can detect these types of patterns, and then the data could be synthesized for this doctor, for this type of patients with similar contexts and presented to the doctor to take quick and effective decisions.

In another example, a 19 year old lady with a kid—unmarried—history of abortion and abuse comes to the ER at a hospital, the system should automatically take into account risks associated and provide risk stratification in terms of suggesting to perform at least certain tests relating to abuse, abortion—etc.

In some implementations, the system should automatically pick up variations in the data or changes in the pattern of synthesis of data and compare those against what was expected and presented is upfront to the doctor to take actions, rather than the doctor figuring out the issue and treating reactively.

An object of the invention is to provide a system and method to provide a system for electronic medical and health records.

Another object of the invention is to provide a system and method for electronic medical and health records, which aids a doctor in identifying and quickly reviewing correct medical information and it also aids doctor to take decisions (computer-aided decisions) with a patients profile including profile fields, which relate tons, weights, measurements, centered around the patient's electronic medical record.

Yet another object of the invention is to provide a system and method to improve health care quality.

Still another object of the invention is to provide a system and method for recording at least a facet of doctor-patient interaction/visit.

An additional object of the invention is to provide a system and method for providing a touch based, click based, voice based or gesture based recording of at least a facet of doctor-patient interaction/visit.

Yet an additional object of the invention is to provide an intuitive system and method for recording a doctor-patient interaction/visit.

Still an additional object of the invention is to provide an intelligent system and method for recording a doctor-patient interaction/visit.

Another additional object of the invention is to provide a system and method, which is context aware so that it understands a doctor correctly, in relation to a doctor-patient interaction, in terms of pre-defined parameters.

Yet another additional object of the invention is to provide a system and method so that it understands the patient correctly, in relation to a doctor-patient interaction, in terms of pre-defined parameters.

Still another additional object of invention is to provide a system and method so that it understands the patient's current and previous medical records and histories correctly in terms of pre-defined parameters.

Yet another additional object of the invention is to provide a system and method so that it understands the doctor-patient interaction correctly in terms of pre-defined parameters.

Yet an additional object of the invention is to provide a system and method so that it understands the location correctly, in relation to a doctor-patient interaction, in terms of pre-defined parameters.

Still an additional object of the invention is to provide a system and method so that it understands the demographic correctly, in relation to a doctor-patient interaction, in terms of pre-defined parameters.

Yet an additional object of the invention is to provide a system and method so that it understands how the doctor is interacting with the patient and documenting in the patient centered electronic medical record system in terms of pre-defined parameters.

Yet an additional object of the invention is to provide a system and method so that it understands how the doctor is interacting with the patient and ordering in the patient centered electronic medical record system in terms of pre-defined parameters.

Still another additional object of the invention is to provide a system and method so that it understands the current condition or state of the patient while documenting in the patient centered electronic medical record system in terms of pre-defined parameters.

Yet an additional object of the invention is to provide a system and method so that it understands which data set (e.g. vitals, lab results, notes, orders, med administration records, past history, and the like) of the medical record should be promoted of the patient while documenting in the patient centered electronic medical record system in terms of pre-defined parameters.

Still another additional object of the invention is to provide a system and method so that it understands which actions or entities (e.g. add a particular problem, suggest a particular test, and the like) of the medical record should be promoted of the patient while documenting or ordering in the patient centered electronic medical record system in terms of pre-defined parameters.

Another additional object of the invention is to provide an intelligent and intuitive system and method to be configured and designed so that a doctor is enabled and empowered to interact with the system in a context-aware manner.

Yet another object of the invention is to make a system and method, for a doctor-patient interaction, context-aware and context-ready for a doctor to interact with it.

Still another additional object of the invention is to provide a system and method so that it understands how to render the synthesized information in real time to suit to the doctor's style of practicing while documenting in the patient centered electronic medical record system in terms of pre-defined parameters.

An additional object of the invention is to provide a system and method, which is easy to use and understand for doctors as well as for patients, thereby increasing user adaptability.

For the purposes of this specification, the term, 'doctor' would include without limitations doctor, doctors, physicians, specialists, super specialists, dentists, surgeons, physiologists, psychiatrists, hospitalists, physiotherapists, medics, medical practitioners, medicos, nurses, nurse practitioners, physician assistants, paramedics, midwifes, clinical staff, and the likes of hospital related or healthcare related persons who deal with patients.

For the purposes of this specification, a 'tap' is defined as a touch or a haptic contact or haptic engagement (whether discrete or continuous) or a click or a gesture, in response to which a pre-defined task or action takes place.

For the purposes of this specification, the term, 'care management', is meant to include actions, set of procedure and protocols adhered in a healthcare environment, which may include, but is not limited to scheduling, patient registration, patient onboarding, patient related document management, patient account management, billing, claims' processing, illness management, diagnosis, prognosis, examination, tests, results, interconnecting various nodes in the healthcare ecosystem, notifications and alarms, and the like.

FIG. 1 illustrates a schematic block diagram of the smart synthesizer system 100. In some implementations. In some implementations, the smart synthesizer system 100 includes a profile configuration mechanism (PCM) 102 adapted to define, configure, and render a patient profile. Each patient profile includes profile fields, which are to be populated with profile data items and parameters relating to these profile data items, hereinafter called profile data parameters. Each of the profile data items are tagged and weighted as per relevant context.

Typically, a patient's profile includes profile fields which relate to demographics, medical history, previous encounters, physicians, problems, diagnosis, allergies, vitals, signs, weights, measurements, growth chart, lines and tubes, intake and output measurements, immunizations and schedule, labs, microbiology, pathology, administered medications, home medications, notes (progress notes, nursing notes, other clinically relevant notes), outstanding orders, diagnostic results (reports, images, and the like), code status, respiratory treatment, family history, social history, previous surgical and/or hospitalization history, any other specialty specific history, risk scores, various assessments, current complaints, adverse reactions, current context (relating to season, epidemic, location, travel, genetics, race, ethnicity and the like), discharge summaries, visit summaries, genomic data of the patient, role of a user, department and specialty, care setting, and the like important event notifications.

In some implementations, each of these profile items corresponds to a context, which is further used in this system and method in order to synthesize a context-aware rendition of patient summary.

In some implementations, the smart synthesizer system 100 includes a set of knowledge/reference databases (KDB) 108. This set of knowledge/reference databases 108 includes multiple fields, which are populated. These fields are knowledge/reference fields. These knowledge/reference fields correlate with profile fields in one or more ways. Data in these knowledge/reference fields refer to knowledge/reference data items. The knowledge/reference fields as well as knowledge/reference data items are updateable as and how the system and method iteratively learns, using artificial intelligence, real time data capture from doctor patient interactions, machine-learning techniques pertaining to a doctor and/or the doctor-patient interaction/visit. Further, these knowledge/reference data items are used to 'synthesize' the existing knowledge/reference data items in order to obtain synthesized knowledge/reference databases 110 in order to render them in a correlation fashion in synchronism with 'profile fields' such that 'rendered' profile data items are obtained and served as an output.

In some implementations, each of the profile data fields are correlated with knowledge/reference fields.

In some implementations, the knowledge database, data items may include inputs from journals, websites, case studies, previous medical records, clinical trials, evidence based medicine data, clinical decision support system related data, population health data, and the like. Initially, these data items are structured using pre-defined rules of structuring and association in relation with pre-defined structured matrices such as UMLS or SNOMED terminologies. These rules are auto-learned, auto-updated intelligently, over time. Various aspects of Natural Language Processing and Machine Learning techniques are used to create these knowledge databases. NLP is used to break down text (e.g. data from journals, textbooks, articles, case studies, previous medical records, web material, data from wearables, sensors, IoT devices, other medical devices, patient medical records, physician documentation/notes and the like) into various forms of data items like conditions, problems, findings, symptoms, medications, allergies, medical equipment, medical events, procedures, orders and the like and then are referenced, indexed, tagged, with cross-references with other data items.

In some implementations, the smart synthesizer system 100 includes a specialty-specific mapping mechanism 112 configured to map doctor specialties and their clinical and data workflows in relation with the set of the synthesized knowledge/reference databases 110. In some implementations, the specialty-specific mapping mechanism 112 reads input items from a pre-determined specialty database and correlatively synthesizes the synthesized knowledge/reference databases 110 into specialty-specific synthesized knowledge/reference databases 114. This is done by a mechanism wherein pertinent fields of specialty are picked, weight-assigned, and thereby mapped.

In some implementations, the set of specialty-specific synthesized knowledge/reference databases 114 includes specialty mapped databases, characterized, in which, at least a database includes fields and data items that are contextually relevant to a pre-defined specialty. Many such pre-defined specialty-specific databases can be built which have correlating specialty-specific fields and specialty-specific data items.

In some implementations, the smart synthesizer system 100 includes a weight assignment mechanism 104 that is configured to assign weights to items in a set consisting of profile fields, profile data items, profile data parameters, knowledge/reference data items and the like. These weights are dynamic in nature. Weights assignment is determined in relation to determined context. Depending upon weight assignment, a profile is rendered. Weight assignment is sought by determination of frequency of use, a latest use, determination of various heat maps used to understand usage and behavior, context settings like location, specialty, current condition of the patient, current of frequency and use of profile data items and/or knowledge/reference data items and the like.

In some implementations, the smart synthesizer system 100 includes a rendering mechanism 106 that is configured to render the system in a context-aware view for a doctor-patient interaction based on pre-defined inputs. Only context relevant data is rendered.

In some implementations, for a given patient profile, the rendering mechanism 106 renders a version of this system and method which is pertinent to the doctor in terms of at least an input selected from asset of inputs consisting of location related inputs, disease related inputs, patient profile related inputs, doctor profile related inputs, specialty related inputs, and the like.

Furthermore, the rendering mechanism 106 may render a version of this system with similar patients with similar signs, symptoms, complaints, disease group, demographics, or previous history.

Furthermore, the rendering mechanism 106 may render an interactive time-line view of this system for a doctor-patient interaction. In some implementations, the rendering mechanism 106 is configured to render an observation profile, which is a function of inputs from the profile configuration mechanism, the set of specialty-specific synthesized knowledge/reference databases, and weight assignment mechanism 104.

In some implementations, an observation profile includes changes in vitals, inputs, outputs in response to change in dosage of prescribed medicine, in response to change in filtering parameters for labs, vitals, diagnostics, and the like. In this embodiment, dosage values for patient are obtained from the patient profile configuration mechanism, standard laboratory values are obtained from the specialty-specific synthesized knowledge/reference databases 114, instantaneous values are obtained from a doctor-patient interaction correlating to the patient profile configuration mechanism. In response to these inputs, the rendering mechanism 106 is configured to assign weights in relation to a determined context and display changes in vitals, intake output, labs or similar data in an empirical format as well as in a predictive format.

In some implementations, the rendering mechanism 106 is configured to render a paraphrased note, which is a function of inputs from the profile configuration mechanism, the set of specialty-specific synthesized knowledge/reference databases 114, and weight assignment mechanism 104 along with natural language processing. In some implementations, a doctor-patient interaction can be converted into a paraphrased note and into actionable items using natural language processing.

In some implementations, the rendering mechanism 106 is configured to render a discharge summary, which is a function of inputs from the profile configuration mechanism, the set of specialty-synthesized knowledge/reference databases 114, and weight assignment mechanism 104 in relation to a doctor-patient interaction. In some implementations, a discharge summary relates to pertinent data of a patient.

In some implementations, the rendering mechanism 106 includes a filtering mechanism in order to filter out and retain data based on structure relationships and artificial intelligence pertaining to context awareness and doctor profile and doctor behavior.

In some implementations, the pre-defined inputs are selected from a set of inputs consisting of defined patient profile, defined doctor specialty, doctor location, patient location, defined doctor profile, and the like. Additional inputs may be defined in order to make this system and method more intelligent.

In some implementations, the profile defining mechanism is correlated to an exodus dataset configured to store exodus data. Additionally, the profile defining mechanism is correlated to a genomic dataset configured to store genomic data.

In some implementations, the smart synthesizer system 100 includes an information database that is configured to store journal information relating to diseases and treatment plans, case studies' information relating to diseases and treatment plans. Each aspect of information in the information database is parsed to be broken down into items of content. These items of content can be data or metadata and are made available to be associated or correlated with various other database and processing or rendering mechanisms of this system.

In some implementations, the smart synthesizer system 100 includes a doctor location determination mechanism that is configured to identify location of a doctor assessing the smart synthesizer system 100. Typically, this is a relation to a doctor-patient interaction/visit. These locations factor in type of care settings, seasons, external condition, seriousness of the condition of the patient, and the like.

In some implementations, the smart synthesizer system 100 includes at least a database relating to evidence based guidelines. Typically, this database includes or correlates to at least a database relating to treatment protocols. In addition, additionally, this database includes or correlates to at least a database relating to treatment pathways.

In some implementations, the smart synthesizer system 100 includes a role-specific system. Rendition and synthesis is dependent on role of a user accessing the system and method of this system. The databases and rules are defined per roles in order to activate this module.

In some implementations, the smart synthesizer system 100 may include databases/datasets, which, further includes symptoms, examinations, vitals, object data, history data, findings' data, and the like. In some implementations, the smart synthesizer system 100 provides a system and method for classifying these databases/datasets into specialty—specific dataset [e.g., cardio, gynecology, and the like] into a constantly evolving database/dataset based on global, local, and hyperlocal updates. Furthermore, the smart synthesizer system 100 renders a view for a doctor-patient interaction/visit to reduce the time taken for a doctor to view patient summary and document an encounter, place orders, and to aid the doctor with decision-making.

In some implementations, a user may provide user input through any suitable input device or input mechanism such as but not limited to a keyboard, a mouse, a joystick, a touchpad, a virtual keyboard, a virtual data entry user interface, a virtual dial pad, a software or a program, a scanner, a remote device, a microphone, a webcam, a camera, a fingerprint scanner, a cave, pointing stick, and the like.

In some implementations, the systems and methods can be practiced using any electronic device. The smart synthesizer 100 includes an electronic device that is selected from any device capable of processing or representing data to a user and providing access to a network or any system similar to the internet, wherein the electronic device may be selected from but not limited to, personal computers, tablet computers, mobile phones, laptop computers, palmtops, portable media players, and personal digital assistants. In an embodiment, the computer readable medium data storage unit or data storage device is selected from a set of but not limited to USB flash drive (pen drive), memory card, optical data storage discs, hard disk drive, magnetic disk, magnetic tape data storage device, data server and molecular memory.

The process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously, in parallel, or concurrently.

Although a few implementations have been described in detail above, other modifications are possible. For example, while a client application is described as accessing the delegate(s), in other implementations the delegate(s) may be employed by other applications implemented by one or more processors, such as an application executing on one or more servers. In addition, the logic flows depicted in the FIG- URES do not require the particular order shown, or sequential order, to achieve desirable results. In addition, other actions may be provided, or actions may be eliminated, from the described flows, and other components may be added to, or removed from, the described systems. Accordingly, other implementations are within the scope of the following claims.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying FIGURES do not necessarily require the particular order shown, or sequential order, to achieve desirable results. In certain implementations, multitasking and parallel processing may be advantageous.

What is claimed is:

1. A computer-implemented method comprising:
   identifying profile fields of a patient profile;
   identifying profile data items and profile data parameters for each profile field;
   generating a synthesized context-aware rendition of a patient summary from the profile data items and the profile data parameters, wherein the generating includes:
      determining a context of a patient, wherein the context includes at least one of a patient geographical location, a current season, or a patient travel history,
         wherein the context of the patient is determined in real time based on data received from one or more devices, and
      dynamically determining weighting assignments for the profile data items, and the profile fields in relation to the context;
   populating the profile fields with the profile data items;
   rendering, in real time, the synthesized context-aware rendition of the patient summary in a context-aware view including an interactive time-line view for a doctor-patient interaction, wherein only context relevant data is rendered;
   capturing real-time data from the doctor-patient interaction; and
   detecting patterns in the real-time data of the doctor-patient interaction to iteratively improve the rendering of synthesized context-aware renditions for doctor-patient interactions of patients with contexts that are similar to the context of the patient.

2. The computer-implemented method of claim 1, further comprising:
   in response to determining the weighting assignments in relation to the context, assigning weights to the profile data items, the profile data parameters, and knowledge/reference data items.

3. The computer-implemented method of claim 2, wherein determining the weighting assignments is determined based on a frequency of use, a latest use, determination of various heat maps to understand usage and behavior, location, specialty, and current condition of the patient.

4. The computer-implemented method of claim 3, further comprising:
   generating the interactive time-line view for the doctor-patient interaction from an observation profile.

5. The computer-implemented method of claim 4, wherein the observation profile changes in vitals, inputs, outputs in response to change in dosage of prescribed medicine, in response to change in filtering parameters for labs, vitals, and diagnostics.

6. The computer-implemented method of claim 1, further comprising:
   determining a location of a doctor corresponding to the patient profile assessing a smart synthesizer system, wherein factors in determining the location of the doctor include care settings, seasons, external conditions, and seriousness of the condition of the patient.

7. A system comprising:
   one or more computers and one or more storage devices storing instructions that are operable, when executed by the one or more computers, to cause the one or more computers to perform operations comprising:
   identifying profile fields of a patient profile;
   identifying profile data items and profile data parameters for each profile field;
   generating a synthesized context-aware rendition of a patient summary from the profile data items and the profile data parameters, wherein the generating includes:
      determining a context of a patient, wherein the context includes at least one of a patient geographical location, a current season, or a patient travel history,
         wherein the context of the patient is determined in real time based on data received from one or more devices, and
      dynamically determining weighting assignments for the profile data items, and the profile fields in relation to the context;
   populating the profile fields with the profile data items;
   rendering, in real time, the synthesized context-aware rendition of the patient summary in a context-aware view including an interactive time-line view for a doctor-patient interaction, wherein only context relevant data is rendered;
   capturing real-time data from the doctor-patient interaction; and detecting patterns in the real-time data of the doctor-patient interaction to iteratively improve the rendering of synthesized context-aware renditions for doctor-patient interactions of patients with contexts that are similar to the context of the patient.

8. The system of claim 7, further comprising:
in response to determining the weighting assignments in relation to the context, assigning weights to the profile data items, the profile data parameters, and knowledge/reference data items.

9. The system of claim 8, wherein determining the weighting assignments is determined based on a frequency of use, a latest use, determination of various heat maps to understand usage and behavior, location, specialty, and current condition of the patient.

10. The system of claim 9, further comprising:
generating the interactive time-line view for the doctor-patient interaction from an observation profile.

11. The system of claim 10, wherein the observation profile changes in vitals, inputs, outputs in response to change in dosage of prescribed medicine, in response to change in filtering parameters for labs, vitals, and diagnostics.

12. The system of claim 7, further comprising:
determining a location of a doctor corresponding to the patient profile assessing a smart synthesizer system, wherein factors in determining the location of the doctor include care settings, seasons, external conditions, and seriousness of the condition of the patient.

13. A non-transitory computer-readable medium storing software comprising instructions executable by one or more computers which, upon such execution, cause the one or more computers to perform operations comprising:
identifying profile fields of a patient profile;
identifying profile data items and profile data parameters for each profile field;
generating a synthesized context-aware rendition of a patient summary from the profile data items and the profile data parameters, wherein the generating includes:
determining a context of a patient, wherein the context includes at least one of a patient geographical location, a current season, or a patient travel history, wherein the context of the patient is determined in real time based on data received from one or more devices, and
dynamically determining weighting assignments for the profile data items, and the profile fields in relation to the context;
populating the profile fields with the profile data items;
rendering, in real time, the synthesized context-aware rendition of the patient summary in a context-aware view including an interactive time-line view for a doctor-patient interaction, wherein only context relevant data is rendered;
capturing real-time data from the doctor-patient interaction; and
detecting patterns in the real-time data of the doctor-patient interaction to iteratively improve the rendering of synthesized context-aware renditions for doctor-patient interactions of patients with contexts that are similar to the context of the patient.

14. The computer-readable medium of claim 13, further comprising:
in response to determining the weighting assignments in relation to the context, assigning weights to the profile data items, the profile data parameters, and knowledge/reference data items.

15. The computer-readable medium of claim 14, wherein determining the weighting assignments is determined based on a frequency of use, a latest use, determination of various heat maps to understand usage and behavior, location, specialty, and current condition of the patient.

16. The computer-readable medium of claim 15, further comprising:
generating the interactive time-line view for the doctor-patient interaction from an observation profile.

17. The computer-readable medium of claim 16, wherein the observation profile changes in vitals, inputs, outputs in response to change in dosage of prescribed medicine, in response to change in filtering parameters for labs, vitals, and diagnostics.

18. The computer-readable medium of claim 13, further comprising:
determining a location of a doctor corresponding to the patient profile assessing a smart synthesizer system, wherein factors in determining the location of the doctor include care settings, seasons, external conditions, and seriousness of the condition of the patient.

19. The computer-readable medium of claim 13, further comprising:
storing, in an information database, journal information relating to diseases and treatment plans for the diseases, and case studies' information relating to the disease and treatment plans.

20. The computer-readable medium of claim 17, further comprising:
displaying, on the interactive time-line view, the changes in vitals, intake output, labs, or similar data in an empirical format and a predictive format.

21. The computer-readable medium of claim 13, wherein the context includes the patient geographical location.

22. The computer-readable medium of claim 13, wherein the weighting assignments are based on usage of the profile data items and the profile fields.

23. The computer-readable medium of claim 13, wherein the one or more devices includes at least one of an Internet of Things (IoT) device, a wearable device, or other sensor.

* * * * *